United States Patent [19]

Hudeček et al.

[11] Patent Number: 4,656,236

[45] Date of Patent: Apr. 7, 1987

[54] TERPOLYMERS HAVING THE CHARACTER OF HYDROGELS

[75] Inventors: Slavko Hudeček; Iva Hudečková; Jaroslava Otoupalová; Pavel Čefelín, all of Prague, Czechoslovakia

[73] Assignee: Ceskoslovenska akademie ved, Czechoslovakia

[21] Appl. No.: 823,371

[22] Filed: Jan. 28, 1986

[30] Foreign Application Priority Data

Jan. 28, 1985 [CS] Czechoslovakia ............... 569-85

[51] Int. Cl.$^4$ .................................................. C08F 26/08
[52] U.S. Cl. ..................................... 526/264; 523/105; 523/111; 526/301
[58] Field of Search ............... 525/455, 920; 526/264, 526/301; 523/105, 111; 524/500, 539, 548

[56] References Cited

U.S. PATENT DOCUMENTS

| | | | |
|---|---|---|---|
| 4,129,709 | 12/1978 | Lorenz et al. ...................... | 525/920 |
| 4,424,305 | 1/1984 | Gould et al. ....................... | 525/455 |
| 4,521,546 | 6/1985 | O'Connor et al. ................. | 525/455 |
| 4,584,354 | 4/1986 | Hudecek et al. ................... | 525/455 |

*Primary Examiner*—Paul R. Michl
*Attorney, Agent, or Firm*—Leydig, Voit & Mayer

[57] ABSTRACT

This invention relates to terpolymers which are capable of forming hydrogels having very good compatibility with living tissues and may be used as substitutes for damaged tissues, as in the form of implants and various prostheses. The terpolymers are comprised of an oligourethane having an average molecular weight from 1200 to 3000, 2-hydroxyethyl(meth)acrylate or 2-hydroxypropyl(meth)acrylate, and N-vinylpyrrolidone.

3 Claims, No Drawings

TERPOLYMERS HAVING THE CHARACTER OF HYDROGELS

The invention pertains to terpolymers having the character of hydrogels.

The term "hydrogels" is generally understood to mean gels containing water, regardless of their chemical structure, or, in a narrower sense of this name, the gels derived from polymers and copolymers of methacrylate esters which contain one hydroxyl group in the side chain (Encyclopedia of Polymer Science and Technology—H. F. MARK, N. G. GAYLORD ed., Vol. 15, p. 276, Wiley-Interscience, New York 1971). The chemical skeleton of these hydrogels is formed mainly from poly(2-hydroxyethyl methacrylate) and its homologues suitably crosslinked with covalent chemical bonds, predominantly by means of ethylene dimethacrylate (Czechoslovak Patent No. 91,918 of 1959 and U.S. Pat. No. 2,976,576 of 1961). In spite of numerous advantages, these hydrogels have also some shortcomings. The question is, above all, their relatively low ability to bind water (up to 30 wt.-% at utmost) at relatively low mechanical properties (e.g. the shear modulus ranges from 0.13 to 0.16 Pa) depending on the degree of crosslinking, which, on the other hand, negatively affects the swelling capacity. Also their long-termed compatibility with living organisms proved insufficient, in contrast to the former optimistic views. The transport of oxygen through this type of hydrogels is rather low.

The above said relatively serious shortcomings led to the endeavour for their removal by modification or copolymerization with N-vinylpyrrolidone, which should lead to the enhanced uptake of water and also to a better compatibility with living organisms. Thus, for example, the Japan Patent No. 5-4, 072-288 (1979) describes the preparation of copolymer of 2-hydroxypropyl methacrylate with N-vinylpyrrolidone by a two-stage copolymerization with an optional addition of a multifunctional crosslinking agent. The British Patent No. 2,088,390 (1982) describes the multistage preparation of a copolymer of N-vinylpyrrolidone with alkyl(meth)acrylate in the presence of a crosslinking agent represented by allyl methacrylate, triallyl cyanurate, or triallyl isocyanurate. In both cases, the application of resulting products is expected in the production of hydrophilic contact lenses. A disadvantage of the described procedures consists in the combined technique used: in the first case, the radical initiation is combined with UV irradiation. Another shortcoming is the application of crosslinking agents giving rise to covalent chemical bonds which are highly mechanically unstable in swelling processes.

The above described shortcomings and disadvantages are overcome in terpolymers having the character of hydrogels, wherein the said terpolymers consist of 5-20 wt.-% of oligourethane with a terminal double bond, having the average molecular weight 1200 to 3000 and the general formula

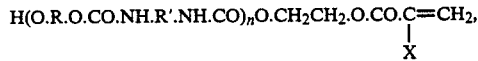

where R corresponds to the used diol and R' to the used diisocyanate, and X is H or $CH_3$, 5-60 wt.-% of 2-hydroxyethyl(meth)acrylate or 2-hydroxypropyl(meth)acrylate, and 32-90 wt.-% of N-vinylpyrrolidone.

A method for preparation of the said terpolymers consists in the radical polymerization of the mixture of oligourethane with a terminal double bond and the average molecular weight 1200-3000, hydroxyalkyl(meth)acrylate and N-vinylpyrrolidone by a commonly known procedure up to the conversion of at least 70% related to the total initial charge.

The oligourethane with a terminal double bond and the molecular weight 1200 to 3000 has the character of macromonomer, i.e. it is able to react with another conventional comonomer giving rise to graft copolymers, where grafts are formed just by the said oligourethane (Czechoslovak Patent No. 223,409). Concerning the chemical structure, which is completely different than the structure of backbone chain formed, according to the invention, from a pair of other comonomers and determined, with respect to the chemical character, by their reactivity ratio, a phase separation occurs during the copolymerization reaction. Microdomains are formed, which give the base to a physical network having several fundamental differences in comparison to a chemical network formed by covalent bonds. In the case of oligourethanes, which are marked by their high tendency to form organized structures, sometimes even crystalline structures, the microdomains have the character of thermally reversible bonds; the network is broken by heating above the melting temperature or the temperature of transition from the glassy to plastic state and the system returns to the original state by cooling. Another characteristic feature of these physical networks is their relatively high elasticity which is able to keep the whole system undisturbed even at large volume changes occurring in swelling processes, whereas mechanical damage (breaking) occurs in the case of covalent linkages.

The oligourethane according to the invention with a terminal double bond and the character of macromonomer is prepared by the reaction of aliphatic, aromatic or alkylaromatic diisocyanates and aliphatic low-molecular-weight diols ($C_2$-$C_4$) according to the Czechoslovak Patent No. 723,409. The terminal unsaturated double bond is introduced into the oligourethane molecule by means of the reaction with 0.03 to 0.25 mole of hydroxyalkyl(meth)acrylate on 1 mole of diisocyanate according to the above refered Czechoslovak Patent. The oligourethanes have the following structure, which was confirmed by IR and $^1$H-NMR spectroscopy:

where R corresponds to the used diol and R' to the used diisocyanate and X is H or $CH_3$.

The terpolymer with composition 5 to 20 wt.-% of oligourethane (macromonomer), 5 to 60 wt.-% of hydroxyethyl(meth)acrylate or 2-hydroxypropyl(meth)acrylate and 30 to 90 wt.-% of N-vinylpyrrolidone is prepared by a radical copolymerization and the commonly known procedure, i.e. either in the presence of initiators based on peroxides, peroxocarbonates, azo compounds, and redox systems or by UV irradiation, and the like, up to the conversion of at least 70% calculated on the initial charge.

Hydrogels based on the terpolymers prepared according to the invention are obtained by immersion the terpolymers into distilled water and swelling to the equilibrium state. Water has to be changed because soluble components (unreacted monomers, homopolymer of N-vinylpyrrolidone) are extracted into it at the same time. The hydrogels prepared in this way contain 40 to 85 wt.-% of water and exhibit relatively suitable mechanical properties (see Table II and IV), which give the evidence that the network structure remained undisturbed even at the volume changing by 50 to 490%.

The hydrogels based on the terpolymers prepared according to the invention have a very good compatibility with living tissues owing to their chemical composition and are therefore suitable above all for substitution of damaged tissues, as implants and various prostheses.

The invention is further illustrated in several examples of performance, without limiting its scope to them.

EXAMPLE 1

Preparation of oligourethane (macromonomer) with molecular weight 2300

Hexamethylenediisocyanate (82.4 ml; NCO content 98.3% of theory), 9.15 ml of 2-hydroxyethyl methacrylate and 1,5 ml of tetrabutyltin were charged into a glass kettle with volume 1000 ml provided with a jacket connected to a thermostated bath, a reflux condenser with a calcium chloride seal, an inlet of nitrogen, and a thermometer. The mixture was heated to 50° C. for 2 h under stirring in the atmosphere of nitrogen and then 300 ml of dimethylformamide was added. After homogenization, it was added 53 g of 2,2'-oxy(diethanol) dissolved in 300 ml of dimethylformamide containing 4.5 ml of tetrabutyltin. The mixture was allowed to react for further 6 hours. The product was then precipitated by pouring the reaction mixture into 8 l of distilled water under stirring and the precipitate was left in water overnight at ambient temperature. The precipitate was filtered, weshed with water and dried in vacuum to the constant weight.

It was obtained 108 g of dry powdery product, which average molecular weight was determined from the content of terminal double bonds (11 mol.%) by means of NMR.

EXAMPLE 2

Preparation of terpolymers I-III and of hydrogels therefrom

A series of three terpolymers was prepared with the oligourethane obtained according to example 1. Their composition and amounts of starting components are given in Table I. The starting mixtures were homogenized and poured between flat glasses 15×15 cm provided with a poly(tetrafluoroethylene) coating and a frame from silicone rubber which served as a distance insertion piece. The polymerization was carried out in a thermostated oven at 50°±2° C. for 48 hours. The resulting plates 1 mm thick were removed from the mold and allowed to swell in the excess of distilled water, which was changed several times.

The hydrogels obtained by equilibrium swelling had water content given in Table II. Test pieces were then cut from the hydrogel plates and used for the measurement of tensile strength, elongation and shear modulus. The results are also presented in Table II.

TABLE I

Composition and initial charges for the preparation of terpolymers I-III using the oligourethane prepared according to example 1

| | Terpolymer | | | | | |
|---|---|---|---|---|---|---|
| | I | | II | | III | |
| | % | g | % | g | % | g |
| Oligourethane | 5.0 | 1.0 | 10.0 | 2.0 | 15.0 | 3.0 |
| N—vinylpyrrolidone | 47.5 | 9.5 | 45.0 | 9.0 | 42.5 | 8.5 |
| HEMA | 47.5 | 9.5 | 45.0 | 9.0 | 42.5 | 8.5 |
| ABIN | 0.1 | 0.02 | 0.1 | 0.02 | 0.1 | 0.02 |

HEMA: 2-hydroxyethyl methacrylate;
ABIN: 2,2'-azobis(isobutyronitrile).

TABLE II

Mechanical properties of hydrogels based on terpolymers I-III

| Terpolymer | Water content % | Tensile strength MPa | Elongation % | Shear modulus MPa |
|---|---|---|---|---|
| I | 70 | 0.31 ± 0.04 | 260 ± 32 | 0.077 |
| II | 59 | 0.60 ± 0.04 | 203 ± 20 | 0.132 |
| III | 54 | 0.99 ± 0.12 | 180 ± 30 | 0.265 |

EXAMPLE 3

Preparation of oligourethane (macromonomer) with $M_n = 2800$ based on diphenylmethane diisocyanate The glass kettle described in example 1 was charged with 60 g of 4,4'-methylenebis(phenylisocyanate) (MDI), 440 g of dimethylformamide and 4.68 g of 2-hydroxyethyl methacrylate (HEMA). The mixture was heated under nitrogen atmosphere to 50° C. and kept at this temperature for 2 hours. Then, the mixture of 15.26 g of 2,2'-oxydiethanol (diethylene glycol=DEG) and 8.47 g of 1,4-butanediol (BD) was added. The reaction was continued for 4 hours.

The molar ratio of initial components was MDI:HEMA:DEG:BD = 1.0:0.15:0.6:0.4. On completion of the reaction, the reaction mixture was cooled to ambient temperature and the product was precipitated in 10 l of distilled water under vigorous stirring and worked out similarly as in example 1. After drying, 85 g (98% of theory) of powdery macromonomer was obtained which had $M_n = 2827$ (determined by the terminal-group method by means of $^1$H-NMR).

EXAMPLE 4

Preparation of terpolymers IV-VIII and of hydrogels therefrom

The product prepared according to example 3 was used in the synthesis of terpolymers IV-VIII, for which the initial batches are given in Table III. The resulting plates 1 mm thick were immersed in the excess of distilled water for several days and water was changed several times. The hydrogel plates obtained were used for cutting the test pieces for measurement of some physical and mechanical properties (see Table IV).

TABLE III

Composition and initial charges for the preparation of terpolymers IV-VIII based on the oligourethane according to example 3

| Terpolymer | Oligourethane | | N—vinyl-pyrrolidone | | HEMA | | ABIN | Extractable compds. % |
|---|---|---|---|---|---|---|---|---|
| | % | g | % | g | % | g | g | |
| IV | 5 | 0.2 | 47.5 | 1.90 | 47.5 | 1.90 | 0.004 | 25 |
| V | 10 | 4.0 | 45 | 18.0 | 45 | 18.0 | 0.04 | 27 |

TABLE III-continued

Composition and initial charges for the preparation of terpolymers IV–VIII based on the oligourethane according to example 3

| Ter-poly-mer | Oligoure-thane % | g | N—vinyl-pyrrolidone % | g | HEMA % | g | ABIN g | Extract-able compds. % |
|---|---|---|---|---|---|---|---|---|
| VI | 12.5 | 2.5 | 43.75 | 8.75 | 43.75 | 8.75 | 0.02 | 15 |
| VII | 15 | 0.3 | 42.5 | 0.85 | 42.5 | 0.85 | 0.002 | 14 |
| VIII | 20 | 0.4 | 40 | 0.9 | 40 | 0.9 | 0.002 | 17 |

TABLE IV

Properties of hydrogels prepared from terpolymers IV–VIII (composition cf. Tab. III) by equilibrium swelling in water

| Ter-polymer | Water content % | Tensile strength MPa | Elongation % | Shear modulus MPa |
|---|---|---|---|---|
| IV | 57 | 0.515 ± 0.03 | 220 ± 20 | 0.114 |
| V | 67 | 1.13 ± 0.04 | 200 ± 10 | 0.216 |
| VI | 51 | 1.88 ± 0.13 | 215 ± 20 | 0.251 |
| VII | 50 | 1.77 ± 0.11 | 170 ± 15 | 0.344 |
| VIII | 40 | 1.43 ± 0.14 | 85 ± 7 | 0.605 |

EXAMPLE 5

Preparation of macromonomer of the oligourethane type with $M_n$ 1760 based on diphenylmethanediisocyanate and of terpolymer therefrom The initial molar ratio was in this case 0.15 HEMA/1.0 MDI/1.0 1,4-butanediol. A 50-ml glass flask, furnished with a stirrer, thermometer, nitrogen inlet and reflux condenser with a calcium chloride seal, was charged with 6.0 g of MDI and 44 ml of dimethylformamide. After 5 minutes, 0.468 g of HEMA was added. The mixture was heated in the stream of dry nitrogen for 3 hours and then 2.14 g of 1,4-butanediol was added under stirring and heating was continued for another 5 hours.

The reaction mixture was cooled and poured into 1000 ml of distilled water under vigorous stirring. The resulting precipitate was allowed to stand for 24 hours in water, filtered, washed and dried in vacuum to a constant weight. The yield of dry powdery product was 8.28 g, i.e. 96% of theory.

This oligourethane was used in the preparation of terpolymers having compositions given in Table V. The polymerization was carried out in glass ampoules at 50° C. 2,2'-Azobis(isobutyronitrile) was used as an initiator for terpolymers IX, X and XII and dibenzoyl peroxide for XI and XIII, always in the amount of 0.1 wt.-%.

TABLE V

Composition of terpolymers IX–XIII (wt. - %)

| Ter-poly-mer | Ol-igoure-thane | N—vinyl-pyrro-lidone | HEMA | HEA | HPMA | Extract-able compds. |
|---|---|---|---|---|---|---|
| IX | 10 | 10 | 80 | — | — | 15 |
| X | 10 | 45 | 22.5 | 22.5 | — | 14 |
| XI | 10 | 45 | — | 45 | — | 28 |
| XII | 10 | 45 | — | — | 45 | 23.5 |
| XIII | 10 | 45 | — | — | — | 26 |

HEMA: 2-hydroxyethyl methacrylate;
HEA: 2-hydroxyethyl acrylate;
HPMA: 2-hydroxypropyl methacrylate.

The hydrogels were obtained by immersion the terpolymers into distilled water until they swell to equilibrium and had the following water content (in wt.-%):

| IX | 43 | XII | 48 |
|---|---|---|---|
| X | 55 | XIII | 41 |
| XI | 58 | | |

EXAMPLE 6

Preparation of terpolymer XIV

A beaker was charged with the following monomers: Macromonomer according to example 1: 0.2 g (i.e. 5 wt.-%) 2-hydroxyethyl methacrylate: 0.2 g (i.e. 5 wt.-%) N-vinylpyrrolidone: 3.6 g (i.e. 90 wt.-%)

The monomers were homogenized and 0.004 g (0.1 wt.-%) of azobis(isobutyronitrile) was added to the mixture. After its dissolution, the mixture was placed in a glass ampoule, bubbled dissolution, the mixture was placed in a glass ampoule, bubbled through with nitrogen, and the ampoule was sealed. The polymerization conditions were the same as in the preceding example. The terpolymer gave by swelling in water the hydrogel having the equilibrium water content 83%.

EXAMPLE 7

Preparation of terpolymer XV

The following components were mixed in a glass beaker:

0.717 g of oligourethane according to example 1
3.24 g of N-vinylpyrrolidone
3.24 g of 2-hydroxyethyl methacrylate
0.007 g of 2,2'-azobis(isobutyronitrile).

The mixture was homogenized and poured into a flat poly(tetrafluoroethylene) mould, which was set in the horizontal position by means of a water-level. The mould was covered with a poly(methyl methacrylate) plate furnished with a nitrogen inlet and the whole assembly was irradiated with a UV-light source (Mikrolux-Chirana) for 20 hours from a 25 cm distance. The resulting milky turbid hard foil gave by swelling to equilibrium a pliable plate containing 60 wt.-% of water.

Testing of compatibility with living tissues

To perform the tests of compatibility with the living organism, 60 test pieces from the terpolymer of type V in the swollen state, having the shape of a disk of diameter 15 mm, were sterilized in a sterilizer and installed subcutaneously into the back of rats of WISTAR breed of the same sex, according to the earlier described method (1,2) keeping all rules of sterility. The total number of rats was 60. The samples were withdrawn always from 10 rats after 10, 30, 60, 90 and 180 days since implantation, the implant with surrounding tissue was fixed with 10% formaldehyde and embedded in paraffin. Paraffin slices underwent the treatment according to Gieson and then according to Masson.

It was found, in comparison with a reference sample, that the terpolymer is nontoxic and well compatible with living tissue, as no histological changes have been observed.

We claim:
1. A terpolymer capable of forming a hydrogel made by polymerizing

(1) from about 5 to about 20 weight percent of an oligourethane having a terminal double bond and an average molecular weight of about 1200 to about 3000, of the general formula

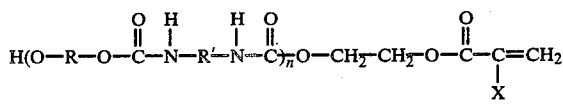

wherein R is a diol residue, R' is a diisocyanate residue, X is H or CH₃, and n is an integer selected from the group consisting of those integers which result in a molecular weight for the oligourethane within the range of about 1200 to abut 3000;

(2) from about 5 to about 60 weight percent of a monomer selected from the group consisting of 2-hydroxyethyl acrylate, 2-hydroxyethyl methacrylate, 2-hydroxypropyl acrylate, and 2-hydroxypropyl methacrylate; and (3) from about 30 to about 90 weight percent of N-vinylpyrrolidone.

2. A hydrogel comprising the terpolymer of claim 1 and from about 40 to about 85 weight percent of water, based on the total weight of the hydrogel.

3. A method for preparing a terpolymer capable of forming a hydrogel comprising polymerizing under free-radical polymerization conditions, (1) from about 5 to about 20 weight percent of an oligourethane having a terminal double bond and an average molecular weight of about 1200 to about 3000, of the general formula

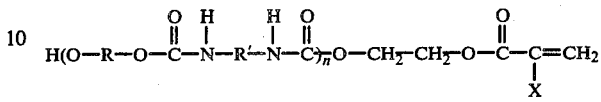

wherein R is a diol residue, R' is a diisocyanate residue, X is H or CH₃, and n is an integer selected from the group consisting of those integers which result in a molecular weight for the oligourethane within the range of about 1200 to about 3000;

(2) from about 5 to about 60 weight percent of a monomer selected from the group consisting of 2-hydroxyethyl acrylate, 2-hydroxyethyl methacrylate, 2-hydroxypropyl acrylate, and 2-hydroxypropyl methacrylate; and (3) from about 30 to about 90 weight percent of N-vinylpyrrolidone until at least about 70% by weight of the monomers have been converted into terpolymer.

* * * * *